(12) United States Patent
Barwell et al.

(10) Patent No.: US 8,607,612 B2
(45) Date of Patent: Dec. 17, 2013

(54) SENSOR CALIBRATION

(71) Applicant: Lightship Medical Limited, London (GB)

(72) Inventors: Nicholas Paul Barwell, Coventry (GB); Peter Edgley, Oxfordshire (GB); Alasdair Allan Mackenzie, Buckinghamshire (GB); William Paterson, Oxfordshire (GB); Barry Colin Crane, Oxfordshire (GB)

(73) Assignee: Lightship Medical Limited, London (GB)

( * ) Notice: Subject to any disclaimer, the term of this patent is extended or adjusted under 35 U.S.C. 154(b) by 0 days.

(21) Appl. No.: 13/686,484

(22) Filed: Nov. 27, 2012

(65) Prior Publication Data

US 2013/0083820 A1   Apr. 4, 2013

(30) Foreign Application Priority Data

Aug. 3, 2011   (GB) .................................. 1113435.0

(51) Int. Cl.
- *G01K 15/00* (2006.01)
- *G01N 33/66* (2006.01)
- *G01N 33/543* (2006.01)

(52) U.S. Cl.
CPC ............ *G01N 33/66* (2013.01); *G01N 33/5438* (2013.01)
USPC .................... 73/1.01; 374/1; 374/3; 73/865.6

(58) Field of Classification Search
USPC ........................................... 73/1.01; 374/1, 3
See application file for complete search history.

(56) References Cited

U.S. PATENT DOCUMENTS

| | | | |
|---|---|---|---|
| 4,818,361 | A | 4/1989 | Burgess et al. |
| 4,861,728 | A | 8/1989 | Wagner |

(Continued)

FOREIGN PATENT DOCUMENTS

| | | | | |
|---|---|---|---|---|
| CA | 1329017 | | 5/1994 | |
| JP | 2002350395 | A * | 12/2002 | ........... G01N 27/416 |

(Continued)

OTHER PUBLICATIONS

Tierney et al., Determination of Glucose Levels Using a Functionalized Hydrogel—Optical Fiber Biosensor: Toward Continuous Monitoring of Blood Glucose in Vivo, Analytical Chemistry, May 1, 2009, vol. 81, No. 9.*

(Continued)

*Primary Examiner* — Hezron E Williams
*Assistant Examiner* — Alexander Mercado
(74) *Attorney, Agent, or Firm* — Fish & Richardson P.C.

(57) ABSTRACT

A method of calibrating a reversible-binding sensor for detecting an analyte includes:
- (i) varying the temperature of a first calibration solution from a first temperature ($T_1$) to a second temperature ($T_2$) while the first calibration solution is in contact with a sensing region of the sensor;
- (ii) determining the sensor output for the first calibration solution as a function of temperature;
- (iii) varying the temperature of a second calibration solution from a third temperature ($T_3$) to a fourth temperature ($T_4$) while the second calibration solution is in contact with the sensing region, the second calibration solution having a concentration of analyte which is different from that of the first calibration solution;
- (iv) determining the sensor output for the second calibration solution as a function of temperature; and
- (v) using the determined sensor output from steps (ii) and (iv) to calibrate the sensor.

22 Claims, 6 Drawing Sheets

(56) References Cited

U.S. PATENT DOCUMENTS

| | | | |
|---|---|---|---|
| 4,889,407 | A | 12/1989 | Markle et al. |
| 4,941,308 | A | 7/1990 | Grabenkort et al. |
| 5,012,809 | A | 5/1991 | Shulze |
| 5,047,627 | A | 9/1991 | Yim et al. |
| 5,137,833 | A | 8/1992 | Russell |
| 5,185,263 | A | 2/1993 | Kroneis et al. |
| 5,329,804 | A | 7/1994 | Germany et al. |
| 5,482,981 | A | 1/1996 | Askari et al. |
| 5,503,770 | A | 4/1996 | James et al. |
| 5,511,408 | A | 4/1996 | Yoshioka et al. |
| 5,512,246 | A | 4/1996 | Russell et al. |
| 5,642,278 | A * | 6/1997 | Wang et al. ............... 700/29 |
| 6,011,984 | A | 1/2000 | Van Antwerp et al. |
| 6,627,177 | B2 | 9/2003 | Singaram et al. |
| 6,682,938 | B1 | 1/2004 | Satcher et al. |
| 7,470,420 | B2 | 12/2008 | Singaram et al. |
| 8,088,097 | B2 | 1/2012 | Markle et al. |
| 8,141,409 | B2 | 3/2012 | Crane et al. |
| 2002/0128546 | A1 | 9/2002 | Silver |
| 2005/0223828 | A1* | 10/2005 | Olin ............... 73/866.5 |
| 2006/0083688 | A1* | 4/2006 | Singaram et al. .......... 424/9.6 |
| 2006/0108218 | A1 | 5/2006 | Gephart et al. |
| 2008/0188725 | A1 | 8/2008 | Markle et al. |
| 2008/0305009 | A1 | 12/2008 | Gamsey et al. |
| 2009/0018418 | A1 | 1/2009 | Markle et al. |
| 2009/0018426 | A1* | 1/2009 | Markle et al. ............... 600/365 |
| 2009/0023222 | A1* | 1/2009 | Wu et al. ............... 436/95 |
| 2010/0280184 | A1 | 11/2010 | Crane |
| 2010/0305413 | A1 | 12/2010 | Paterson |
| 2011/0044576 | A1 | 2/2011 | Crane |
| 2012/0096918 | A1 | 4/2012 | Crane et al. |
| 2012/0156793 | A1 | 6/2012 | Higgs |

FOREIGN PATENT DOCUMENTS

| | | |
|---|---|---|
| WO | WO96/01989 | 1/1996 |
| WO | WO00/43536 | 7/2000 |
| WO | WO01/42473 | 6/2001 |
| WO | WO2007/011691 | 1/2007 |
| WO | WO2008/001091 | 1/2008 |
| WO | WO2008/141243 | 11/2008 |
| WO | WO2009/106805 | 9/2009 |
| WO | WO2010/133831 | 11/2010 |
| WO | WO2011/097586 | 8/2011 |

OTHER PUBLICATIONS

Baldini and Mignani. "Optical-Fiber Medical Sensors," MRS Bulletin, May 2002, 5 pages.

International Search Report and Written Opinion in International Application No. PCT/GB2012/051188, mailed Aug. 7, 2012, 11 pages.

Lindner et al., Design and applications of biomimetic anthraquinone dyes: purification of calf intestinal alkaline phosphates with immobilized terminal ring analogues of C.I. reactive Blue 2, *Journal of Chromatography*, 1989, 473(1):227-240.

"Optical Glucose Sensor Holds Promise for Diabetics and Intensive Care Patients," ScienceDaily, Mar. 17, 2004 <http://web.archive.org/web/20040404161607/ http://www.ScienceDaily.com/releases/2004/03/040317073529.htm>, 6 pages.

Search Report in Great Britain Application No. GB1113435.0, dated Nov. 2, 2011, 4 pages.

Tierney et al. "Determination of Glucose Levels Using a Functionalized Hydrogel-Optical Fiber Biosensor: Toward Continuous Monitoring of Blood Glucose in Vivi," 2009, *Anal. Chem.*, 81(9):3630-3636 (Abstract only).

Yoon and Czamik. "Fluorescent chemosensors of carbohydrates. A means of chemically communicating the binding of polyols based on chelation-enhanced quenching," *J. Am. Chem. Soc.* 1992, 114:5874-5875.

* cited by examiner

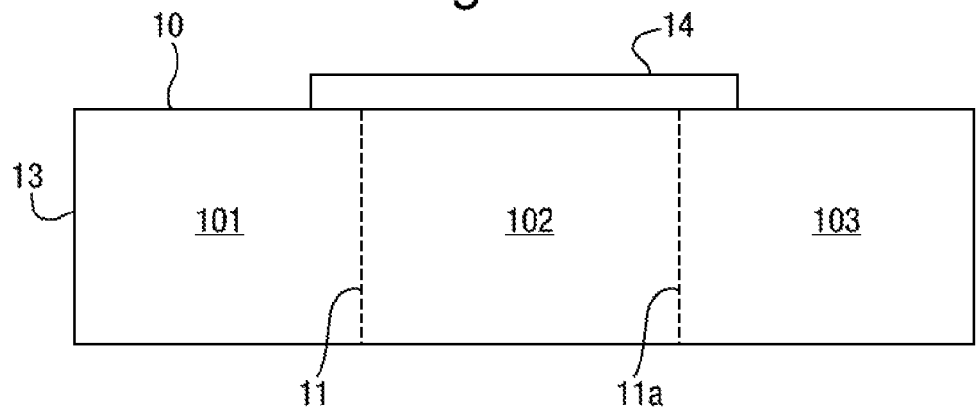
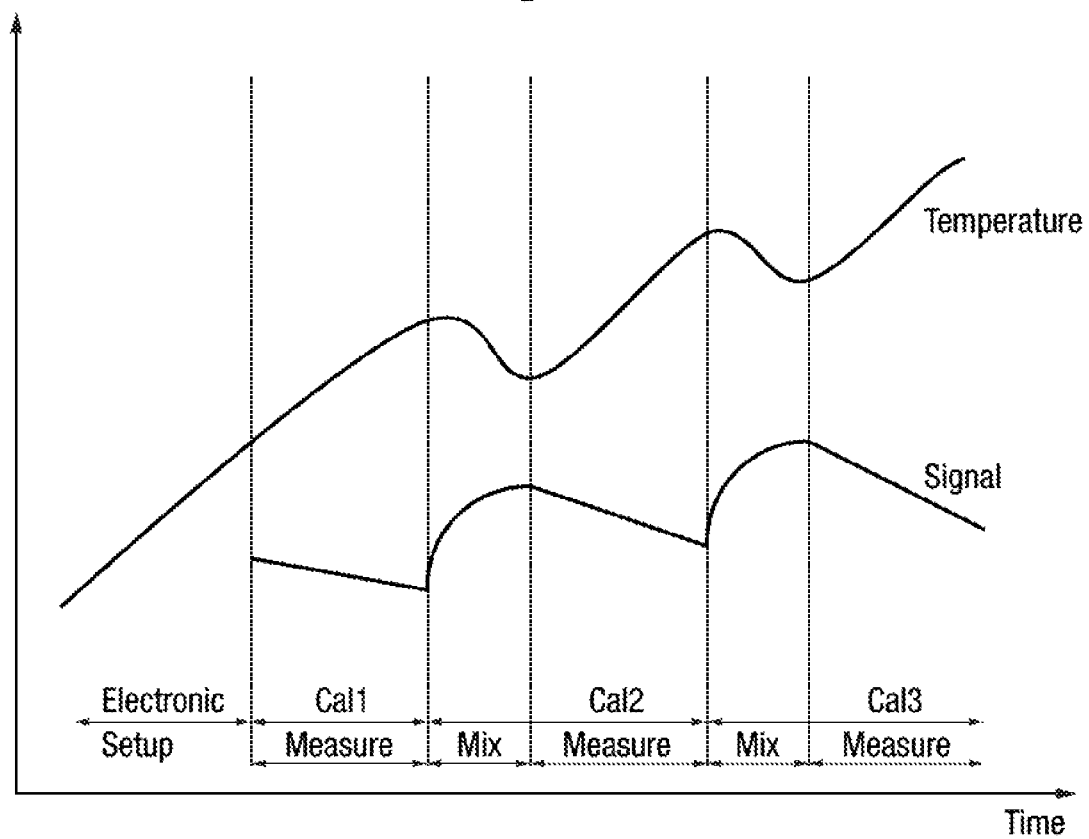

Fig. 5

| FHU Calibration Results | | |
|---|---|---|
| mmol | signal | TC |
| 0 | 1.0000 | -0.0220 |
| 13.4 | 1.2502 | -0.0339 |
| 23.4 | 1.3873 | -0.0386 |
| | | |
| $I_0$ | 1.0000 | |
| $I_\infty$ | 2.4538 | |
| K | 0.0155 | |
| $Mod_{5mM}$ | 9.48 | |
| | | |
| α | -0.0220 | |
| β | -17.8015 | |

| FHU Calibration Results | | |
|---|---|---|
| mmol | signal | TC |
| 0 | 1.0000 | -0.0148 |
| 14.1 | 1.3989 | -0.0412 |
| 28.2 | 1.6000 | -0.0402 |
| | | |
| $I_0$ | 1.0000 | |
| $I_\infty$ | 2.2096 | |
| K | 0.0349 | |
| $Mod_{5mM}$ | 15.23 | |
| | | |
| α | -0.0148 | |
| β | -26.0293 | |

| FHU Calibration Results | | |
|---|---|---|
| mmol | signal | TC |
| 0 | 1.0000 | -0.0205 |
| 13.1 | 1.8677 | -0.0513 |
| 27 | 2.3059 | -0.0700 |
| | | |
| $I_0$ | 1.0000 | |
| $I_\infty$ | 3.4925 | |
| K | 0.0408 | |
| $Mod_{5mM}$ | 29.68 | |
| | | |
| α | -0.0205 | |
| β | -24.6896 | |

| FHU Calibration Results | | |
|---|---|---|
| mmol | signal | TC |
| 0.0 | 0.6620 | -0.0098 |
| 14.1 | 0.9261 | -0.0273 |
| 28.2 | 1.0592 | -0.0266 |
| | | |
| $I_0$ | 0.6620 | |
| $I_\infty$ | 1.4588 | |
| K | 0.03526 | |
| $Mod_{5mM}$ | 15.28 | |
| | | |
| α | -0.014804 | |
| β | -26.15886 | |

| Temp / °C | Variable Temperature Calibration | | Fixed Temperature Calibration | |
|---|---|---|---|---|
| | [Glc] / mM | Error % | [Glc] / mM | Error % |
| 32 | 4.9 | -3.8 | 7.6 | 50.6 |
| 33 | 4.9 | -3.5 | 7.0 | 37.0 |
| 34 | 4.9 | -3.3 | 6.3 | 23.4 |
| 35 | 4.9 | -3.1 | 5.6 | 9.9 |
| 36 | 4.9 | -2.8 | 4.9 | -3.7 |
| 37 | 4.9 | -2.6 | 4.2 | -17.3 |
| 38 | 5.0 | -2.4 | 3.5 | -30.9 |
| 39 | 5.0 | -2.1 | 2.8 | -44.4 |
| 40 | 5.0 | -1.9 | 2.1 | -58.0 |

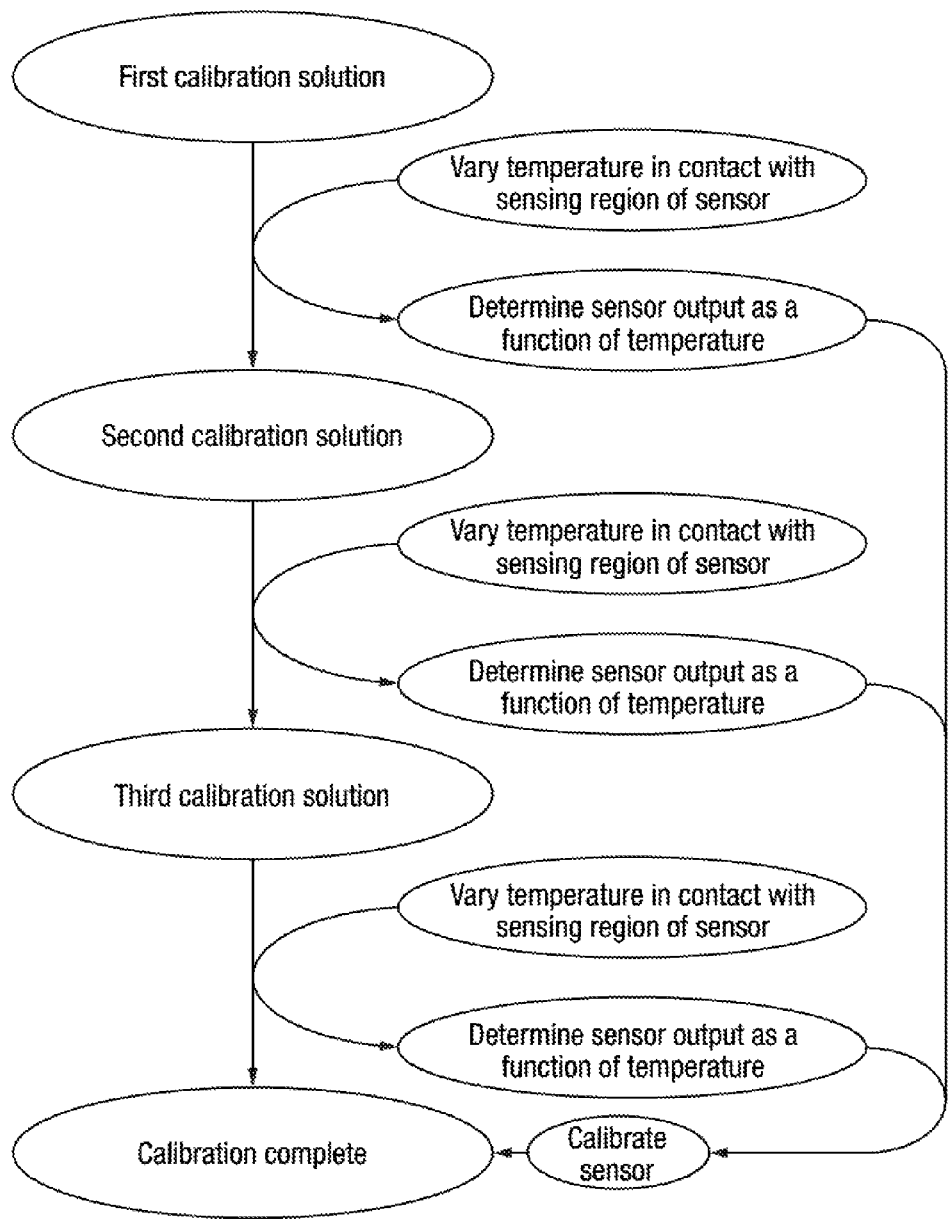

SENSOR CALIBRATION

CLAIM OF PRIORITY

This application claims priority under 35 USC §119(b) to PCT Application No.: PCT/GB2012/051188 filed on May 25, 2012 which claims priority to GB1113435.0 filed on Aug. 3, 2011 and to U.S. Provisional Application Ser. No. 61/490,951, filed on May 27, 2011, the entire contents of which are hereby incorporated by reference.

TECHNICAL FIELD

This document describes a method of calibrating a sensor for detecting an analyte. In particular embodiments, the method of calibrating a sensor can be used at the point of use.

BACKGROUND

The usual aim in developing a chemical sensor or biosensor is to produce a digital electronic signal, whose magnitude depends on the concentration of a specific chemical or set of chemicals (analyte). The sensor usually includes two main components, a chemical or biological part that reacts or complexes with the analyte in question (ideally specifically) to form new chemical or biological products or changes in energy that can be detected by means of the second component, a transducer. The chemical/biological component can be said to act as a receptor/indicator for the analyte. A variety of transduction methods can be used including electrochemical (such as potentiometric, amperometric, conductimetric, impedimetric), optical, calorimetric and acoustic. After transduction the signal is usually converted to an electronic digital signal.

Since the signal generated by the chemical/biological reaction with the analyte is usually dependent not only on the concentration of the analyte but also on the characteristics of the sensor itself, such sensors usually require calibration before they can be utilised quantitatively. The way in which the signal varies with the analyte concentration determines the shape of the calibration curve (signal versus analyte concentration) and may define the number of calibration points. Typical calibration curves can be straight line, exponential, s-shaped, etc. and the principal of calibration applies to all methodologies of transduction for chemical or biological sensors.

Ideally, the sensor should be calibrated just before its use since some sensor characteristics that can affect the calibration curve vary with time (ageing effect). It is often the case that the time between sensor manufacture and use can be many months, so calibration at the point of manufacture can lead to inaccuracies in the end result.

In the case of a medical sensor, an attendant clinician or nurse may be required to perform the calibration whilst maintaining sterility of the sensor. Additional constraints applied by the clinician/nurse are that the calibration process should be simple to perform, ideally invisible to the person performing the calibration, and be quickly completed (preferably in less than 10 minutes). Calibration of many currently available medical sensors requires the clinician/nurse to carry out a number of specific steps which can lead to errors or inaccuracies in the measurement if the process is not followed correctly.

There is therefore a need for a method of calibrating a sensor which avoids the inaccuracies caused by ageing effects, and which is a simple procedure, capable of being carried out at the point of use by an inexperienced user.

SUMMARY

A method of calibrating a reversible-binding sensor for detecting an analyte is described herein. The method includes at least the following steps:
  (i) varying the temperature of a first calibration solution from a first temperature ($T_1$) to a second temperature ($T_2$) while the first calibration solution is in contact with a sensing region of the sensor;
  (ii) determining the sensor output for the first calibration solution as a function of temperature;
  (iii) varying the temperature of a second calibration solution from a third temperature ($T_3$) to a fourth temperature ($T_4$) while the second calibration solution is in contact with the sensing region, the second calibration solution having a concentration of analyte which is different from that of the first calibration solution;
  (iv) determining the sensor output for the second calibration solution as a function of temperature; and
  (v) using the determined sensor output from steps (ii) and (iv) to calibrate the sensor.

The calibration curve for a sensor is typically dependent on temperature. For example, when a sensor detects an analyte by binding reversibly to the analyte, the equilibrium constant for the reversible binding, which is temperature dependent, will affect the calibration curve. Accordingly, if the temperature at which calibration is carried out is not identical to the temperature at which the sensor is used, and no allowance is made for the temperature dependence of the sensor parameters determined during calibration, the calibration parameters may not be accurate. Thus, errors can be introduced in the analyte concentration readings provided by the sensor.

A calibration method for a biological sensor can assume that the measurement is always made at 37° C., and aim to provide a calibration curve suitable for use at that temperature. However, not all patients have precisely the same temperature. This type of calibration can therefore lead to inaccurate results in patients having a temperature of higher or lower than 37° C.

A calibration method for a biological sensor could also require a temperature coefficient to be determined at the point of manufacture. In such methods, temperature coefficients can be determined by carrying out a standard calibration at multiple fixed temperatures, for example 3 fixed temperatures. Thus, such methods may involve (a) taking sensor output readings for a first, second and third calibration solution, each calibration solution having a different analyte concentration and each reading being taken at a first temperature; (b) taking a second set of sensor output readings for the first, second and third calibration solution, each reading in the second set being taken at a second temperature; and (c) taking a third set of sensor output readings for the first, second and third calibration solution, each reading in the third set being taken at a third temperature.

Calibration at multiple fixed temperatures is time consuming, requires stabilisation of the sensor temperature, is difficult to automate and difficult to perform while maintaining sterility of the sensor. Accordingly, it is easier to rely on an average temperature coefficient determined at the point of manufacture for a batch of sensors, and then apply that to the calibration curve for all sensors in that batch. Such an approach has the disadvantage that the average temperature coefficients are not optimised for any particular sensor to which they may be applied. Further, the temperature dependence of a sensor can change over the time elapsed between manufacture and use, which can lead to further inaccuracies due to ageing effects.

The presently described method improves on these methods, and in particular addresses the ageing effects seen in the art by providing a calibration which can be completed entirely at the point of use and which avoids the need to use temperature coefficients generated at the time of manufacture. This is achieved by determining sensor output as a function of temperature for at least two calibration solutions with different concentrations.

In the context of the present disclosure "determining sensor output as a function of temperature" means measuring the rate of change of signal versus temperature. That can be achieved, for example, by taking sensor output readings at each of two or more temperatures, as the temperature of a calibration solution is varied. The output readings and temperatures can then be analysed to determine how a change in temperature affects sensor output for that calibration solution.

This method can thereby determine the parameters required for calibration and their temperature dependence, without extending the calibration time and without needing to stabilise the sensor temperature. This method can be carried out quickly, can be automated, and is suitable for point of use calibration.

In some embodiments, the method further includes:
(vi) varying the temperature of a third calibration solution from a fifth temperature ($T_5$) to a sixth temperature ($T_6$) while the third calibration solution is in contact with the sensing region, the third calibration solution having a concentration of analyte which is different from those of the first and second calibration solutions; and
(vii) determining the sensor output for the third calibration solution as a function of temperature;
wherein step (v) includes using the determined sensor output from steps (ii), (iv) and (vii) to calibrate the sensor.

The third calibration solution can have a different concentration of analyte from the first and second solutions. By determining sensor output as a function of temperature for this third solution, a third set of calibration points can be generated. Since a large number of devices require three point calibration in order to be accurately calibrated with a predetermined calibration algorithm, three point calibration is preferred. If desired, four or more point calibration can be carried out by use of four or more calibration solutions.

Calibration systems are also described. The calibration system includes one or more control modules configured to monitor and/or adjust the temperature, to bring a sensor into contact with a plurality of calibration solutions, and to determine a calibration for a sensor. The system may also include at least one calibration chamber and/or a reversible binding sensor. In some embodiments, the one or more control modules can calibrate the sensor. For example, the one or more control modules can be configured to monitor sensor output and temperature output from the sensor, to supply heat to or remove heat from the calibration chamber, to introduce or change the calibration solution within the calibration chamber (e.g., by adding or diluting analyte) or to move the sensor between a plurality of calibration chambers, and to determine calibration parameters for the sensor based on the data obtained from the calibration run. Accordingly, the one or more control modules are configured to perform the calibration methods described herein.

In one embodiment, steps (i) to (v), and, when used, steps (vi) and (vii), are carried out using one or more control modules, the one or more control modules being configured to contact the sensing region of a reversible binding sensor with consecutive calibration solutions; monitor and/or adjust the temperature of the calibration solutions; and determine sensor output of said sensor as a function of temperature for each of said calibration solutions. The one or more control modules are typically further configured to calibrate the sensor. For the avoidance of doubt, "consecutive calibration solutions" means, firstly, the first calibration solution, secondly, the second calibration solution, and, when used, thirdly, the third calibration solution. The term also includes any subsequent calibration solutions used, e.g. a fourth or fifth calibration solution, in order.

The calibration chamber can include multiple compartments. For example, a first compartment can include a first calibration solution and additional compartments can include amounts of analyte or diluting liquid. The compartments can be separated by water-impermeable dividing materials. By breaking or removing the dividing materials, the calibration solution can be altered into different calibration solutions.

In some embodiments, the calibration chamber can include one or more cutting or piercing tools configured to be advanced to breach dividing materials between the compartments. In some embodiments, the one or more control modules can be configured to advance or activate one or more cutting or piercing tools according to a predetermined calibration procedure.

In some embodiments, a sensor or a sensor region of a sensor can be packaged with a calibration chamber. For example, the sensing region can be positioned within the calibration chamber in order to keep the calibration chamber and the sensor region
sterile prior to and during the calibration process. For example, the sensing region can be positioned within a first compartment of a calibration chamber including a first calibration solution and second and third compartments of the calibration chamber can include analyte (e.g., in solid form). The sensor and the calibration chamber can then be attached to one or more docketing stations including the one or more control modules to run the calibration procedure. In some embodiments, the calibration chamber includes the one or more heating elements or cooling elements that are controlled by the one or more control modules. In other embodiments, heating or cooling elements can be supplied in a docketing station. In some embodiments, the calibration docketing station can be included as part of a device that outputs sensor data.

BRIEF DESCRIPTION OF THE FIGURES

The method is further described below with reference to exemplary embodiments and accompanying drawings in which:

FIGS. 3*a* and 3*b* depict embodiments of the calibration chamber of a sensor kit which kit may contain the sensor to be calibrated using the presently described method.

FIG. 4 depicts schematically temperature and signal changes during an embodiment of the three point calibration method.

FIG. 5 shows data recorded from calibration in Example 1.

FIG. 10 shows a flow chart representing steps involved in an embodiment of the three-point calibration method of the invention.

DETAILED DESCRIPTION

Figure 1:
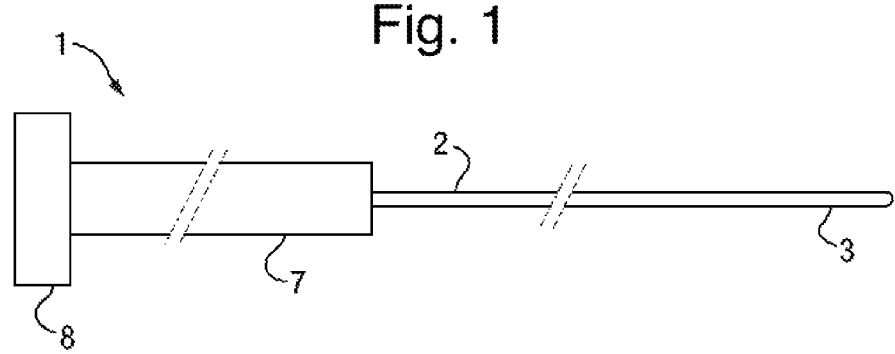
FIG. 1 depicts a sensor which may be calibrated using the presently described method.

The presently described method can be used to calibrate a reversible binding sensor. Typically, in a reversible-binding sensor, sensor output is produced by transducing an effect caused by the analyte reversibly binding to a receptor in the sensing region of the sensor. The reversible binding reaction between the analyte and receptor is typically at chemical equilibrium.

In some embodiments, the analyte reversibly binds to the receptor at an analyte:receptor ratio of 1:1. For such sensors there is a linear relationship between analyte concentration and sensor output at equilibrium.

The presently described calibration technique is suitable for use with any type of reversible-binding sensor. For example, the sensor may be an electrochemical sensor, e.g. a pH sensor. In some embodiments, the sensor is an optical sensor. In an optical sensor, the effect caused by the analyte reversibly binding to the receptor is an optical effect, and typically a luminescent effect. For example, the optical sensor can be a fluorescent sensor, and the sensor can include a fluorophore associated with the receptor. Where a fluorophore is associated with the receptor, this indicates that binding of an analyte molecule to the receptor perturbs the fluorescence of the fluorophore, e.g. its wavelength, intensity or lifetime. Such fluorescent sensors therefore exhibit a change in wavelength, intensity and/or lifetime of the fluorescence when analyte binds to the receptor. Thus, the sensor may detect or quantify the amount of analyte present in a sample by monitoring changes in the wavelength, intensity and/or lifetime of the fluorescence. Typically, the intensity or the lifetime is measured.

In some embodiments, the analyte is glucose. For a glucose sensor, the sensor can include a glucose receptor having a binding site having one or more (e.g. two) boronic acid groups. For example, two boronic acid groups can be present and be separated by a spacer group. When the sensor is exposed to a glucose containing solution, glucose binds to the boronic acid groups and typically forms a 1:1 complex with the receptor. As will be appreciated, however, the presently describe method is suitable for use with a variety of different analytes and their corresponding receptors, to where reversible binding occurs. The skilled person would be able to identify suitable analytes and receptors, but further examples of analyte/receptor pairs include those shown in the Table 1 below:

TABLE 1

| Analyte | Receptor |
|---|---|
| $Cl^-$, $Br^-$ | Katapinands, protonated cryptands, quaternised cryptands |
| $Na^+$, $K^+$ | Crown ethers, cryptands |
| $K^+$ | Valinomycin (selective) |

Calibration

As used herein, the term calibration is used to mean a process including determining parameters (hereinafter called "calibration parameters") which allow sensor output or signal to be related quantitatively to analyte concentration. In some embodiments, at least one calibration parameter is dependent on temperature.

In some embodiments, step (ii) includes determining the sensor output for the first calibration solution at two or more temperatures in a temperature range from $T_1$ to $T_2$; step (iv) includes determining the sensor output for the second calibration solution at two or more temperatures in a temperature range from $T_3$ to $T_4$; and, when steps (vi) and (vii) are used, step (vii) includes determining the sensor output for the third calibration solution at two or more temperatures in a temperature range from $T_5$ to $T_6$.

The number of temperatures at which sensor output is determined for the first, second and/or third calibration solution can be 50 or more, preferably 100 or more, more preferably 150 or more, most preferably 200 or more. A more accurate calibration can be obtained as the number of measurements is increased. For example, the measurements may be obtained by measuring the sensor output for each calibration solution once every second, preferably twice every second, more preferably three times every second and most preferably four times every second over a period of from thirty seconds to two minutes, preferably one minute.

For an invasive sensor, the method can be carried out at a sensor temperature of between 30 and 40° C., i.e. around body temperature. For example, the method can be carried out at a sensor temperature of between 35 and 39° C., and more preferably between 36 and 38° C. For sensors which are not to be used in vivo, calibration can be carried out over a temperature range which reflects the temperature at which the sensor will be used, e.g. around ambient temperature.

In some embodiments, the second calibration solution is formed by mixing the first calibration solution with an amount of analyte, and, when steps (vi) and (vii) are used, the third calibration solution is formed by mixing the second calibration solution with a further amount of analyte. Similarly, the fourth calibration solution if used may be formed by mixing the third calibration solution with a still further amount of analyte. In some embodiments, the second calibration solution is allowed to equilibrate before step (iv) is carried out, and, when steps (vi) and (vii) are used, the third calibration solution can be allowed to equilibrate before step (vii) is carried out. An amount of time needed for the calibration solution to equilibrate can be determined by one of skill in the art and will depend on solubility of the analyte, whether or not mechanical mixing is used, and the response time of the sensor. In some embodiments where a glucose sensor is being calibrated, the calibration solutions are allowed to equilibrate by waiting at least 10 seconds after adding the analyte (e.g., glucose), preferably at least 30 seconds after adding analyte. For example, the calibration solution can be allowed to equilibrate for 1 minute.

In order to minimise the length of time required for calibration to be completed, steps (iv) and, when used, (vii) can be carried out as soon as the solution has equilibrated, i.e. when signal output as a function of temperature becomes of the order expected for a particular analyte:receptor binding ratio. For example, when the analyte:receptor binding ratio is 1:1, signal output is first order as a function of temperature. Thus, equilibration is complete once signal output becomes linear with temperature.

When the analyte is glucose, the glucose which is mixed with the first solution to form the second solution can include both α-glucose and β-glucose. In some embodiments, when the analyte is glucose and steps (vi) and (vii) are used, the glucose which is mixed with the second solution to form the third solution also includes α-glucose and β-glucose. Methods of calibrating glucose sensors using α and β glucose are described in WO 2010/133831, the content of which is incorporated herein in its entirety.

In some embodiments, the calibration includes the following stages (depicted in FIG. 4)

Warmup
Initial temperature increase and automatic electronic setup
First Calibration Solution (cal1): Measure
Measure signal as a function of temperature for first calibration solution at zero analyte. Heating applied ($T_1 \rightarrow T_2$)
Second Calibration Solution (cal2): Mix
Mix first calibration solution with analyte to form second calibration solution and wait for equilibrium with changed analyte concentration. No heat applied ($T_2 \rightarrow T_3$)
Second Calibration Solution (cal2): Measure
Measure signal as a function of temperature for second calibration solution at 5 mmol analyte. Heating applied ($T_3 \rightarrow T_4$)
Third Calibration Solution (cal3): Mix
Mix second calibration solution with analyte to form third calibration solution and wait for equilibrium with changed analyte concentration. No heat applied ($T_4 \rightarrow T_5$)
Third Calibration Solution (cal3): Measure
Measure signal as a function of temperature for third calibration solution at 10 mmol analyte. Heating applied ($T_5 \rightarrow T_6$)

In some embodiments, $T_2$ is greater than $T_1$, $T_4$ is greater than $T_3$, and, when steps (vi) and (vii) are used, $T_6$ is greater than $T_5$. In other words, steps (i), (iii) and, when used, (vi), typically involve heating the calibration solutions. Heating the calibration solution can be a convenient way to provide a temperature gradient.

The ranges $T_1$ to $T_2$, $T_3$ to $T_4$ and, when steps (vi) and (vii) are used, $T_5$ to $T_6$ can be close together in terms of temperature. In some embodiments, the ranges can overlap. In other words $T_3$ can be less than or equal to $T_2$, and, when steps (vi) and (vii) are used, $T_5$ can be less than or equal to $T_4$. In some embodiments, all of the used temperature ranges (e.g., $T_1$ to $T_2$, $T_3$ to $T_4$, and optionally $T_5$ to $T_6$) correspond to the same range which spans all temperatures at which the sensor is likely to be used, e.g. 36-38° C. for an invasive sensor.

Therefore, in some embodiments as depicted in the scheme above, heating occurs during the measurement periods $T_1$ to $T_2$, $T_3$ to $T_4$ and $T_5$ to $T_6$, but heating is stopped (or cooling is applied) during the mixing periods $T_2$ to $T_3$ and $T_4$ to $T_5$. This causes the calibration solution to cool, or maintain substantially the same temperature, during the mixing phase. In some embodiments, cooling of the solution occurs during mixing such that the temperature $T_3$ at which the second measurement phase begins is approximately the same as the temperature $T_1$ at which the first measurement phase begins. Alternatively, the second measurement phase may be started at a higher temperature, such that $T_3$ is greater than $T_1$. Similarly, for a three point calibration, temperature $T_5$ may be approximately equal to, or greater than, $T_3$.

The concentration of analyte in the first calibration solution can be zero. The skilled person would be able to determine suitable concentrations of analyte for the first, second and optional third or further calibration solutions. Typical concentrations should include zero (first analyte solution) and concentrations at the upper and lower end of those which are likely to be measured by the sensor. In the example of calibration of a glucose sensor for use with intensive care patients, a first calibration solution typically has a zero concentration, whilst the second and third calibration solutions typically have concentrations of, for example 5 mmolL$^{-1}$ and 10 mmolL$^{-1}$ respectively. In an alternative embodiment in the case of a glucose sensor, the concentrations of the first, second and third calibration solutions are 0 mmolL$^{-1}$, approximately 15 mmolL$^{-1}$ and approximately 30 mmolL$^{-1}$, respectively. Further alternative concentrations could be selected depending on the type and end use of the sensor.

In some embodiments, the method further includes:
(viii) contacting the sensing region of the sensor with a sample and determining the concentration of analyte in the sample.

The sample may be any fluid which is to be analysed by use of a reversible binding sensor. For example, bodily fluids such as whole blood or plasma may be used as the sample. For an invasive sensor, the sample is typically blood or interstitial fluid. Other samples for non-invasive sensors may also be envisaged such as water samples or food products.

The sensor can be calibrated at the point of use. As used herein, "calibrated at the point of use" means that the time between beginning calibration in step (i) and using the sensor to determine analyte concentration in step (viii) is 24 hours or less. In some embodiments, the time between beginning calibration in step (i) and using the sensor to determine analyte concentration in step (viii) is 12 hours or less, 5 hours or less, or 1 hour or less.

The following description explains how the calibration parameters can be determined for an optical sensor providing fluorescence measurements. The skilled person would be able to adapt this procedure for other types of sensor.

A calibration equation that can be used to relate sensor output to analyte concentration is $$I = \frac{I_0 + k\rho I_\infty}{1 + k\rho} \qquad (1)$$

where I is the sensor output and $\rho$ is the analyte concentration. In this equation there are three parameters that have to be derived from a calibration procedure:

$I_0$ the sensor output at zero concentration
$I_\infty$ the (theoretical) sensor output at infinite concentration
k the modulation constant $I_0$ can be subtracted from both sides of equation (1) to give $$I - I_0 = \frac{k\rho}{1 + k\rho}(I_\infty - I_0)$$

or $$\Delta = \frac{k\rho}{1 + k\rho}\Delta_m \qquad (2)$$

where $\Delta$ is the change in sensor output and $\Delta_m$ is the maximum possible change in sensor output. The change is relative to the sensor output at zero analyte concentration.

Temperature dependent calibration can include two stages, (I) deriving the calibration equation from the receptor-analyte reversible binding chemistry, and (II) applying the equation to determine the calibration parameters.

(I) Deriving the Calibration Equation from the Receptor-Analyte Reversible Binding Chemistry Although the presently described calibration method is not limited to sensors having a receptor:analyte binding ratio of 1:1, the equilibrium of a 1:1 binding process that leads to increased sensor output in the presence of analyte can be represented by

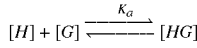

where [H] is the receptor, or host concentration, [G] is the guest (analyte) concentration, and $K_a$ is the association constant of the reaction. Note that although [H] is unknown it is very small compared to $1/K_a$ and it is also small compared to [G] (except at exactly zero analyte concentration).

The association constant of the reaction is related to the equilibrium concentrations by $$K_a = \frac{[HG]}{[H][G]}. \tag{3}$$

The bracket notation for concentration can be replaced by the Greek symbol $\rho$, for example $\rho_g$ instead of [G] and $\rho_h$ instead of [H]. Thus $$K_a = \frac{\rho_c}{\rho_h \rho_g} \tag{4}$$

where $\rho_c$ is the concentration of the complex "host+guest" molecule.
It is possible to write:

$$\rho_g = \rho_{gi} - \rho_c \tag{5}$$

$$\rho_h = \rho_{hi} - \rho_c \tag{5}$$

where $\rho_{gi}$ is the known initial analyte concentration and $\rho_{hi}$ is the unknown initial host concentration.
Substituting (5) and (6) into (4) gives $$K_a = \frac{\rho_c}{(\rho_{gi} - \rho_c)(\rho_{hi} - \rho_c)} \tag{7}$$

Rearranging (7) gives a quadratic equation for the unknown $\rho_c$:

$$\rho_c^2 - (\rho_{gi} + \rho_{hi} + 1/K_a)\rho_c + \rho_{hi}\rho_{gi} = 0 \tag{8}$$

The standard solution of a quadratic gives $$\rho_c = \frac{(\rho_{gi} + \rho_{hi} + 1/K_a) \pm \sqrt{(\rho_{gi} + \rho_{hi} + 1/K_a)^2 - 4\rho_{hi}\rho_{gi}}}{2}$$

and the lower (minus) sign must be taken so that $\rho_c$ tends to zero as the initial host and guest concentrations tend to zero.

Therefore $$\rho_c = \frac{(\rho_{gi} + \rho_{hi} + 1/K_a)}{2}\left[1 - \sqrt{1 - \frac{4\rho_{hi}\rho_{gi}}{(\rho_{gi} + \rho_{hi} + 1/K_a)^2}}\right]$$

Because $K_a\rho_{hi} \ll 1$ the square root term can be expanded to first order $$\rho_c \approx \frac{(\rho_{gi} + \rho_{hi} + 1/K_a)}{2}\left[1 - \left(1 - \frac{2\rho_{hi}\rho_{gi}}{(\rho_{gi} + \rho_{hi} + 1/K_a)^2}\right)\right] \tag{9}$$

$$= \frac{\rho_{hi}\rho_{gi}}{\rho_{hi} + \rho_{gi} + 1/K_a}$$

Again, the fact that $K_a\rho_{hi} \ll 1$ enables the $\rho_{hi}$ term in the denominator of (9) to be dropped, giving $$\frac{\rho_c}{\rho_{hi}} = \frac{K_a\rho_{gi}}{1 + K_a\rho_{gi}} \tag{10}$$

This is in fact the canonical form of the calibration formula, equation (2), which can be re-written $$\frac{\Delta}{\Delta_m} = \frac{k\rho}{1 + k\rho} \tag{11}$$

Comparing equations (10) and (11), the fractional change in sensor output equals the fraction of the host converted to the complex that leads to sensor output. The modulation parameter k can be identified with the chemical association constant $K_a$.

Since the calibration equation can be derived from the chemical balance equation, fitting the data to either should give essentially the same results.

(II) Applying the Calibration Equation to Determine the Calibration Parameters

In equation (10) the right hand side (RHS) has a temperature dependence buried in the $K_a$ term while the left hand side (LHS) has no explicit temperature dependence. The denominator of the LHS is a constant (for a given sensor) while the numerator is the quantity that is (indirectly) measured. The same interpretation can be applied to equation (11): $\Delta$ is the measurement while $\Delta_m$ is a constant for a given sensor.

The denominator of the LHS of equation (11) is: $\Delta_m = I_\infty - I_0$. $I_0$ is known experimentally to be temperature dependent. $I_0$ and $I_\infty$ have the same temperature dependence, due to $I_0$, since $I_\infty = \Delta_m + I_0$. In words, $\Delta_m$ is the fluorescence signal expected when all the host is bound to analyte, and has no temperature dependence. So for $\Delta_m$ we can use nominal calibration temperature values of $I_0$ and $I_\infty$.

The numerator of the LHS of equation (11) is: $\Delta = I - I_0$. The actual measurement is I and the observed temperature dependence of $I_0$ must be allowed for. The temperature dependence of $I_0$ is observed experimentally to be very closely linear and can be approximated:

$$I_0 = [1 + \alpha(T - T_c)]I_{0c} \tag{12}$$

where $\alpha$ is the linear temperature coefficient, $T_c$ is the nominal calibration temperature, and $I_{0c}$ the measured sensor output at $T_c$ and zero analyte The last term whose temperature dependence must be considered is $K_a$ which is expected to be an exponential function of the reciprocal of the absolute temperature: $G=-RT \ln K_a$ where G is the Gibbs free energy and R is the gas constant, or $$K_a \propto \exp\left(-\frac{eV}{k_B T}\right)$$

where V is the energy barrier and $k_B$ is the Boltzmann constant.

One way of writing the energy dependence of $K_a$ in a form suitable for computation is $$K_a = K_{ac}\exp\left[\beta\left(1 - \frac{T_c}{T}\right)\right] \quad (13)$$

where $K_{ac}$ is the association constant at the nominal calibration temperature and $\beta$ is a measure of the Gibbs free energy, or the energy in volts, converted to a non-dimensional constant.

Including all the temperature dependencies by substituting (12) and (13) into (11) we get $$\frac{I - I_0[1 + \alpha(T - T_c)]}{I_\infty - I_0} = \frac{\rho K_a \exp\beta\left(1 - \frac{T_c}{T}\right)}{1 + \rho K_a \exp\beta\left(1 - \frac{T_c}{T}\right)}$$

where the subscript 'c' has been dropped—hereinafter the quantities $I_0$, $I_\infty$, $K_a$ all denote "at the calibration temperature". Thus $$I = I_0[1 + \alpha(T - T_c)] + (I_\infty - I_0)\frac{\rho K_a \exp\beta\left(1 - \frac{T_c}{T}\right)}{1 + \rho K_a \exp\beta\left(1 - \frac{T_c}{T}\right)} \quad (14)$$

If $\alpha$ and $\beta$ were the same for all sensors then a three-point calibration would suffice i.e. the same temperature correction could be applied to all sensors. Since this is not the case a calibration procedure should determine five unknowns ($I_0$, $I_\infty$, $K_a$, $\alpha$, $\beta$) from measurements at two analyte concentrations as a function of temperature.

Throughout calibration the absolute temperature T is always close to $T_c$ i.e. $T/T_c \approx 1$ and so the exponential terms can be expanded to first order $$1 - \frac{T_c}{T} = 1 - \frac{1}{\left(1 + \frac{T - T_c}{T_c}\right)} \approx 1 - \left(1 - \frac{T - T_c}{T_c}\right) = \frac{T - T_c}{T_c}$$

so that the exponential can be expanded $$\exp\beta\left(1 - \frac{T_c}{T}\right) \approx \exp\left(\beta\frac{T - T_c}{T_c}\right) \approx 1 + \beta\frac{T - T_c}{T_c}$$

The numerator in (14) can be expanded further $$1 + \rho K_a \exp\beta\left(1 - \frac{T_c}{T}\right) \approx 1 + \rho K_a\left(1 + \beta\frac{T - T_c}{T_c}\right) =$$

$$(1 + \rho K_a)\left(1 + \frac{\rho K_a \beta}{1 + \rho K_a}\frac{T - T_c}{T_c}\right)$$

so that $$\frac{1}{1 + \rho K_a \exp\beta\left(1 - \frac{T_c}{T}\right)} \approx \frac{1}{(1 + \rho K_a)}\left(1 - \frac{\rho K_a \beta}{1 + \rho K_a}\frac{T - T_c}{T_c}\right)$$

Then (14) becomes $$I = I_0[1 + \alpha(T - T_c)] + (I_\infty - I_0)\frac{\rho K_a}{1 + \rho K_a}\left(1 + \beta\frac{T - T_c}{T_c}\right)\left(1 - \frac{\rho K_a \beta}{1 + \rho K_a}\frac{T - T_c}{T_c}\right)$$

and by dropping second order terms the equation becomes linear in the temperature offset $T - T_c$:

$$I = I_0[1 + \alpha(T - T_c)] + \quad (15)$$

$$(I_\infty - I_0)\frac{\rho K_a}{1 + \rho K_a}\left(1 + \beta\frac{T - T_c}{T_c} - \frac{\rho K_a \beta}{1 + \rho K_a}\frac{T - T_c}{T_c}\right)$$

$$I = I_0 + (I_\infty - I_0)\frac{\rho K_a}{1 + \rho K_a} + I_0\alpha(T - T_c) +$$

$$(I_\infty - I_0)\frac{\rho K_a}{1 + \rho K_a}\left(1 - \frac{\rho K_a}{1 + \rho K_a}\right)\beta\frac{T - T_c}{T_c}$$

$$I = I_0 + (I_\infty - I_0)\frac{\rho K_a}{1 + \rho K_a} + I_0\alpha(T - T_c) +$$

$$(I_\infty - I_0)\frac{\rho K_a}{(1 + \rho K_a)^2}\beta\frac{T - T_c}{T_c}$$

The legitimacy of the expansion of (14) to first order in $T - T_c$ is confirmed by experiment: it has been consistently observed over many batches of sensors that a good straight line fit can always be made to the variation of signal with temperature at constant analyte.

Sensor output is determined as a function of temperature for the first and second calibration solutions:

$$I = I_1 + s_1(T - T_c) \rho = \rho_1 \quad (16)$$

$$I = I_2 + s_2(T - T_c) \rho = \rho_2 \quad (17)$$

The nominal calibration temperature values $I_0$, $I_\infty$, $K_a$ can be found from the intensities $I_1$, $I_2$, $I_3$ by methods known in the art (e.g. those used for fixed-temperature calibration techniques). Equating the slopes of (15) and (16), and of (15) and (17) gives:

$$I_0\alpha + (I_\infty - I_0)\frac{\rho_1 K_a}{(1 + \rho_1 K_a)^2}\frac{\beta}{T_c} = s_1 \quad (18)$$

$$I_0\alpha + (I_\infty - I_0)\frac{\rho_2 K_a}{(1 + \rho_2 K_a)^2}\frac{\beta}{T_c} = s_2 \quad (19)$$

This pair of simultaneous equations can be solved for $\alpha$ and $\beta$:

$$\alpha = \frac{1}{I_0}\frac{s_1\frac{\rho_2 K_a}{(1+\rho_2 K_a)^2} - s_2\frac{\rho_1 K_a}{(1+\rho_1 K_a)^2}}{\frac{\rho_2 K_a}{(1+\rho_2 K_a)^2} - \frac{\rho_1 K_a}{(1+\rho_1 K_a)^2}} = \frac{s_1}{I_0}\left[\frac{1 - \frac{\rho_1}{\rho_2}\frac{s_2}{s_1}\frac{(1+\rho_2 K_a)^2}{(1+\rho_1 K_a)^2}}{1 - \frac{\rho_1}{\rho_2}\frac{(1+\rho_2 K_a)^2}{(1+\rho_1 K_a)^2}}\right] \quad (20)$$

$$\beta = \frac{\frac{(s_2 - s_1)T_c}{I_\infty I_0}}{\frac{\rho_2 K_a}{(1+\rho_2 K_a)^2} - \frac{\rho_1 K_a}{(1+\rho_1 K_a)^2}} = \quad (21)$$

$$\frac{(1+\rho_2 K_a)^2 T_c(s_2 - s_1)}{(I_\infty - I_0)\rho_2 K_a}\left[\frac{1}{1 - \frac{\rho_1}{\rho_2}\frac{(1+\rho_2 K_a)^2}{(1+\rho_1 K_a)^2}}\right]$$

Where $\rho_1=0$, (20) becomes:

$$\alpha = s_1/I_0 \quad (22)$$

and (21) becomes:

$$\beta = \frac{(1+\rho_2 K_a)^2 T_c(s_2 - s_1)}{(I_\infty - I_0)\rho_2 K_a} \quad (23)$$

The three parameters $K_a$, $I_\infty$ and $I_0$ that have to be derived from a calibration procedure can therefore be derived by:
 determining $s_1$ and $s_2$ by fitting measured sensor output and temperature readings to the following linear expressions:

$$I=I_1+s_1(T-T_c)\rho=\rho_1 \quad (16)$$

$$I=I_2+s_2(T-T_c)\rho=\rho_2 \quad (17)$$

using $s_1$ and $s_2$, along with values of $K_a$, $I_\infty$ and $I_0$ which are known for a reference temperature $T_c$, to determine $\alpha$ and $\beta$ with equations (20) and (21):

$$\alpha = \frac{1}{I_0}\frac{s_1\frac{\rho_2 K_a}{(1+\rho_2 K_a)^2} - s_2\frac{\rho_1 K_a}{(1+\rho_1 K_a)^2}}{\frac{\rho_2 K_a}{(1+\rho_2 K_a)^2} - \frac{\rho_1 K_a}{(1+\rho_1 K_a)^2}} = \frac{s_1}{I_0}\left[\frac{1 - \frac{\rho_1}{\rho_2}\frac{s_2}{s_1}\frac{(1+\rho_2 K_a)^2}{(1+\rho_1 K_a)^2}}{1 - \frac{\rho_1}{\rho_2}\frac{(1+\rho_2 K_a)^2}{(1+\rho_1 K_a)^2}}\right] \quad (20)$$

$$\beta = \frac{\frac{(s_2 - s_1)T_c}{I_\infty - I_0}}{\frac{\rho_2 K_a}{(1+\rho_2 K_a)^2} - \frac{\rho_1 K_a}{(1+\rho_1 K_a)^2}} = \quad (21)$$

$$\frac{(1+\rho_2 K_a)^2 T_c(s_2 - s_1)}{(I_\infty - I_0)\rho_2 K_a}\left[\frac{1}{1 - \frac{\rho_1}{\rho_2}\frac{(1+\rho_2 K_a)^2}{(1+\rho_1 K_a)^2}}\right]$$

using $\alpha$ and $\beta$ to determine the values of $K_a$, $I_\infty$ and $I_0$ at the actual calibration temperature T with equations (12) (13) and $I_\infty=I_0+\Delta_m$ (see denominator of LHS of equation (11)).

$$I_0 = [1 + \alpha(T - T_c)]I_{0c} \quad (12)$$

$$K_a = K_{ac}\exp\left[\beta\left(1 - \frac{T_c}{T}\right)\right] \quad (13)$$

Although the preceding derivation of the equations used to calculate the parameters required for calibration are based on an analyte:receptor binding ratio of 1:1, one of skill in the art would be able to derive appropriate equations by analogy with the procedure set out above in order to obtain calibration parameters for equilibrium-based reversible binding sensors in which the analyte:receptor binding ratio is other than 1:1, for example 1:2, 1:3, 1:4, 1:5, 2:1, 2:3, 2:5, 3:1, 3:2, 3:4, 3:5, 4:1, 4:3, 4:5, 5:1, 5:2, 5:3 or 5:4.

Detailed Description of Sensor and Kit for Use in the Method

In some embodiments, the sensor to be calibrated is provided as part of a kit. The kit can also include a calibration chamber and temperature controller. For example, the kit can be arranged such that:
 the first calibration solution is present in a first compartment of the calibration chamber,
 an amount of analyte is present in a second compartment of the calibration chamber,
 the second compartment of the calibration chamber is initially separated from the first compartment of the calibration chamber by a water-impermeable first dividing material, and
 whereby the presently described method is performed using the kit by breaking or removing the first dividing material to form the second calibration solution.

In still further embodiments, the kit can further be arranged such that:
 the calibration chamber further includes a third compartment containing a further amount of the analyte,
 the third compartment is initially separated from the remainder of the calibration chamber by a second water-impermeable dividing material, and
 whereby certain embodiments of the presently described method are performed using the kit by breaking or removing the second dividing material to form the third calibration solution.

The analyte in the second and/or third compartments can be in solid form. For example, glucose can be provided in solid form. In some embodiments, solid glucose is present in a solid form that includes both alpha and beta glucose. When the third compartment of the calibration chamber is present, the glucose in the third compartment can also be provided in solid form (e.g., a solid form that includes alpha and beta glucose).

The sensor can include a temperature sensor. In some embodiments, the sensor includes a thermistor. The temperature sensor can be used to monitor the actual temperature during calibration.

The temperature of the calibration solutions can be varied using a temperature controller. For example, the temperature can be controlled using a heater (e.g., a heating element).

An example of an invasive glucose sensor which can be calibrated using the presently described method is described in detail below. Invasive sensors typically operate in a temperature range of 35-39° C. A sensor can contain a temperature sensor, such that the temperature of the sensor can be determined. A heating element can be provided to vary the temperature within the calibration chamber during calibration. A temperature sensor within the sensor can be used to monitor the actual temperature during calibration. Other sensor calibration methods are described in WO 2008/001091, the content of which is incorporated herein in its entirety. The calibration chamber can include a mixer (e.g., a mixing element or a device that imparts vibration) with which to mix the calibration solutions after the addition of analyte.

Figure 2:
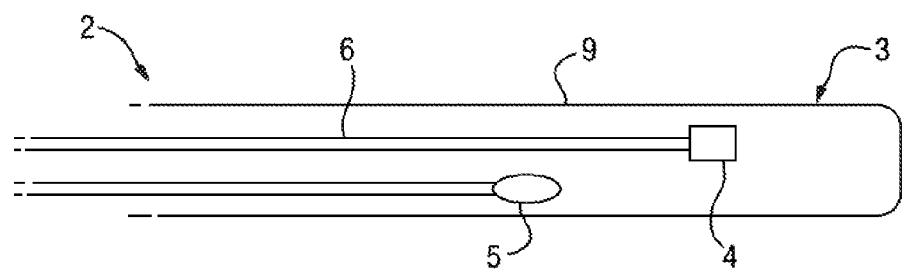
FIG. 2 depicts the sensing region of the sensor of FIG. 1 in more detail.

One particular invasive glucose sensor is based on a fibre optic technique and is depicted in FIG. 1. The sensor 1 includes an insertable tip 2 which is adapted for insertion into a patient, for example insertion into a blood vessel through a cannular. The insertable tip includes a sensing region 3 (depicted in more detail in FIG. 2) in to which the glucose receptor 4, and also a temperature sensor 5, are positioned. The glucose receptor is immobilised on or in an optical fibre 6, such that a signal emitted by the receptor is transmitted through the optical fibre. The optical fibre extends through cable 7 to connector 8, which is adapted to mate with an appropriate monitor (not depicted). The monitor typically includes further optical cable that mates with the connector at one end and at the other bifurcates to connect to (a) an appropriate light source for the optical sensor and (b) a detector for the emitted signal. Electrical connection to the temperature sensor is also provided through connector 8 and appropriate detection equipment is provided by the monitor. The monitor may also comprise the one or more control modules for carrying out the sensing method, as described herein.

The sensing region of the sensor is coated with a membrane 9 which should generally be haemocompatible and allow diffusion of glucose (or other analyte where appropriate) from the surrounding blood or body fluid to the receptor 4.

Receptors for a number of analytes which could be incorporated into such a sensor are known in the art. For example, crown ethers may be used to detect potassium and various enzymes are also useful. In the case of glucose, a useful receptor is a boronic acid compound having a fluorophore. The boronic acid species provides the ability to complex with glucose and the fluorescence emission pattern of the molecule is altered in the presence of glucose, which allows optical detection.

The receptor is typically immobilized to the optical fibre in a hydrogel which allows diffusion of water and glucose to the receptor compound. Cross-linked polyacrylamide or polyhydroxyethylmethacrylate (p-HEMA) are examples of hydrogels that can be used.

Figure 3A:
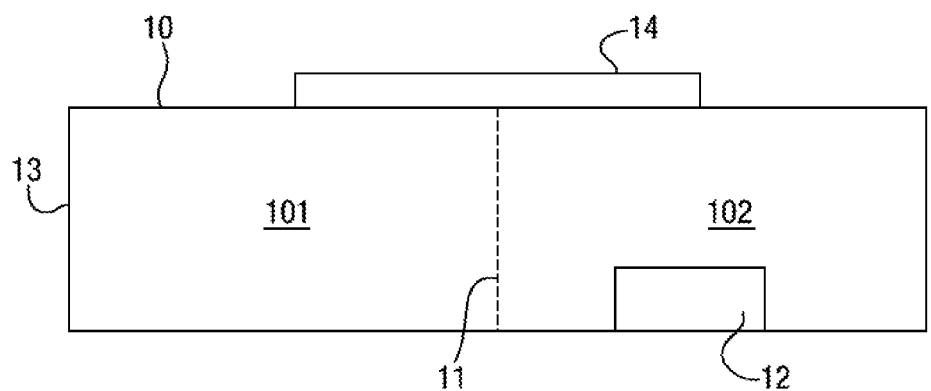

A calibration chamber is depicted in FIG. 3a. The calibration chamber 10 includes two compartments 101 and 102, which are separated by a water-impermeable dividing material 11 e.g. a breakable dividing material. The first compartment 101 contains water or an aqueous solution. Typically, this compartment contains an isotonic solution and does not contain the analyte. Thus, determining the sensor output as a function of temperature for the first calibration solution typically provides a set of readings for zero analyte concentration. However, analyte may be contained in the first compartment, e.g. at low concentration, if desired.

The second compartment contains a source of the analyte 12, e.g. glucose. This may be in the form of a concentrated solution of the analyte or, as depicted at 12 in FIG. 3a, the analyte itself in solid form. Where the analyte is glucose, the second compartment typically contains glucose in solid form (e.g. powder, tablet etc.), whilst the first compartment does not contain glucose. Aqueous solutions of glucose have been found to degrade on sterilisation with either heat or gamma-radiation. Thus, this embodiment has the advantage that no aqueous solution of glucose is present and degradation is minimised. The second compartment may be under inert gas atmosphere (e.g. dry nitrogen) to avoid oxygen-induced irradiation degradation.

Calibration of the sensor can be carried out by exposing the sensing region of the sensor to the first compartment 101 containing the first calibration solution. In one aspect of this embodiment, the sensing region of the sensor is inserted into the first compartment 101. To enable the sensor to be inserted, outer wall 13 of the first compartment is typically at least in part pierceable. For example, the outer wall 13 may be a septum which can be pierced by a needle. The sensor can be inserted into the first compartment through or within the needle. Once the sensing region is in place within the first compartment, the temperature of the first calibration solution is varied by applying heat from heater 14 and the sensor output as a function of temperature is determined for the first calibration solution.

In an alternative aspect of this embodiment, a seal is provided between the sensor and the first compartment. Breaking the seal, e.g. by movement of the sensor or a part of the outer wall 13 of the first compartment, causes the content of the first compartment to flow around the sensor, thus exposing the sensor to the first calibration solution.

The dividing material separating first and second compartments is then broken or removed allowing the contents of these compartments to mix. During this period, heating is generally not applied to the calibration chamber. The dividing material is typically broken or removed without opening the sealed calibration chamber in order to maintain sterility. Thus, the material is broken for example by piercing with a needle inserted into the first compartment through the outer wall 13. In one embodiment, the sensor is inserted into the first compartment within a needle, and the needle, containing the sensor, can then be pushed forwards to rupture the dividing material.

The dividing material may be any material which can be broken, ruptured or removed causing the contents of the first and second compartments to mix. In one embodiment, the dividing material is an elastomeric material which is maintained under tension so that on piercing with a needle the material will be fully ruptured. Natural or synthetic rubbers are examples of such materials. In an alternative embodiment, the material is rigid, but is scored with fracture lines such that on piercing with a needle it readily fractures into components. Plastics and ceramics are examples of suitable rigid materials. Both of these types of dividing material provide a large opening between the first and second compartments, allowing quick mixing of the contents of the compartments. Alternative dividing materials include metal foils (e.g. aluminum foil) which may be coated with plastic.

The dividing material should be impermeable to water and the analyte to avoid leakage between the two compartments of the calibration chamber. In one embodiment, one surface of the dividing material is metallised to assist in preventing water diffusion. The metallised surface is typically in contact with the second compartment which is preferably under an inert gas atmosphere.

In order to speed up mixing of the contents of the first and second compartments (e.g. dissolution of a solid analyte into the water or aqueous solution), physical mixing of the calibration chamber, e.g. agitation or ultra-sonic mixing, may be used or alternatively chemical additives that effervesce can be added to the calibration chamber to provide mixing.

Once the contents of the two compartments are mixed, a second calibration solution is provided having a different concentration of analyte from the first calibration solution. Heat is again applied from heating element 14 and the sensor output as a function of temperature determined from readings taken on this solution therefore provides a second set of calibration points. This, along with a predetermined calibration algorithm, enables a calibration curve to be generated and the sensor to be calibrated. The skilled person would be able to provide appropriate algorithms for calibration of any particular type of sensor given in the light of this disclosure.

Typically, the calibration is carried out by connecting connection 8 of the sensor to a monitor adapted for continuous measurement of the sensor output. The monitor may comprise one or more control modules configured to carry out the calibration method described herein. Thus, as soon as the sensor is exposed to the first compartment of the calibration chamber, the monitor connected and switched on, and the calibration chamber is heated to the starting temperature $T_1$, a first set of readings can be taken. Rupture or breakage of the dividing material is then carried out and the monitor will continually record the sensor output during mixing of the analyte source with the water or aqueous solution of the first compartment. The calibration chamber is not heated during mixing, so that the range of temperatures over which sensor output is recorded for the second calibration solution is close to, and may overlap with, the range of temperatures over which sensor output is recorded for the first calibration solution. Heating is resumed when the sensor output becomes linear due to mixing being complete, and the second set of readings is taken during this second heating phase. The second set of readings can typically be completed within about 5 minutes, preferably about 2 minutes, more preferably about 1 minute, from the start of the calibration process.

In an automated process, one or more of the steps of exposing the sensor to the first compartment and removing or breaking dividing material 11 may be machine-driven. A stepper motor or a stepper motor attached to a lead screw may be used in this regard.

FIG. 3b depicts an alternative calibration chamber suitable for carrying out a 3-point calibration. The chamber includes compartment 101 which typically includes water or an aqueous solution forming the first calibration solution, and compartments 102, 103, which each contain glucose in solid form. Successive rupture of the dividing materials 11, 11a will provide firstly a second calibration solution containing added glucose from compartment 102, and subsequently a third calibration solution additionally containing the glucose from compartment 103. Calibration can therefore be carried out as described above, but with the addition of further steps to determine the sensor output as a function of temperature the third calibration solution. In particular, once the readings for the second calibration solution have been taken, the second dividing material 11a is broken and the contents of the compartments mixed, typically until equilibrium is reached. Heat is again applied from heating element 14 and the sensor output as a function of temperature determined from readings taken on this third solution provide a third set of calibration points. Calibration is then carried out using the first, second and third calibration points.

Example 1

An optical glucose sensor as depicted in FIG. 1 in a calibrator filled with PBS (phosphate buffer solution), which contains two sealed pods of a mixture of α/β glucose 40:60, was inserted into a calibration unit which is capable of stirring and heating the calibration solution. The temperature of the calibration solution was raised to 25° C. and the instrument gains were set. The temperature was increased further and sensor output (cal1 data) was recorded as the temperature was varied between 30 ($T_1$) and 36° C. ($T_2$). The first glucose pod was then burst and once the sensor reached equilibrium (i.e. once the sensor output varied linearly with temperature), sensor output (cal2 data) was recorded as the temperature was varied between 36 ($T_3$) and 38° C. ($T_4$). The second glucose pod was then burst and once the sensor reached equilibrium, sensor output (cal3 data) was recorded between 38 ($T_5$) and 40° C. ($T_6$).

Effect of Modulation

The results of three calibrations with sensors of differing modulation are shown in FIG. 5, the fluorescent intensities at 0 mM glucose (37° C.) have been normalised to 1.

It can be seen from these calibrations that as the modulation of the sensor decreases the value of K also decreases and the values of α and β also vary. This indicates that the sensor must be temperature calibrated at the point of use to minimise errors when measuring the glucose concentration.

Results

Figures 6, 7:
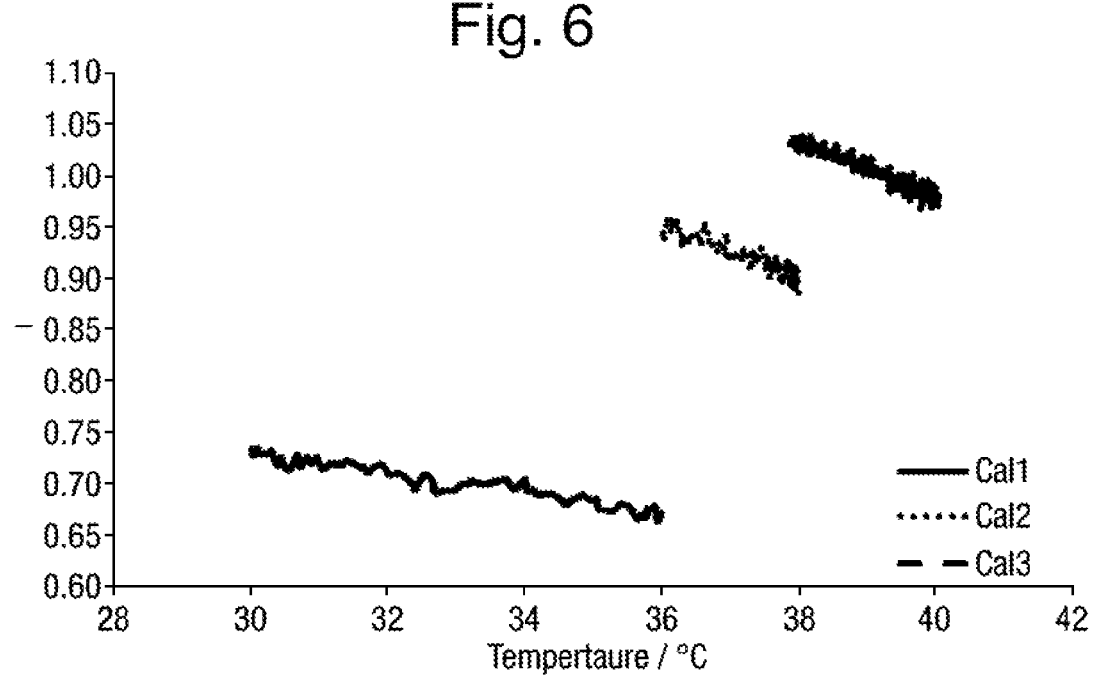
FIG. 6 shows intensity vs. temperature recorded during calibration in Example 1.
FIG. 7 shows the results of calibration in Example 1.

The data recorded from a calibration can be seen in FIG. 6. As expected, the fluorescent intensity (I, y-axis) decreased as the temperature was increased for the three different glucose concentrations, in this case [Glc]=0, 14.1, and 28.2 mmol The gradients of these three calibration points were measured and the intensities for calibration points 1-3 at 37° C. were determined. This allowed calculation of the parameters $I_0$, $I_\infty$ and K at 37° C. and to derive the two temperature dependent constants α and β, FIG. 7.

Figures 8, 9:
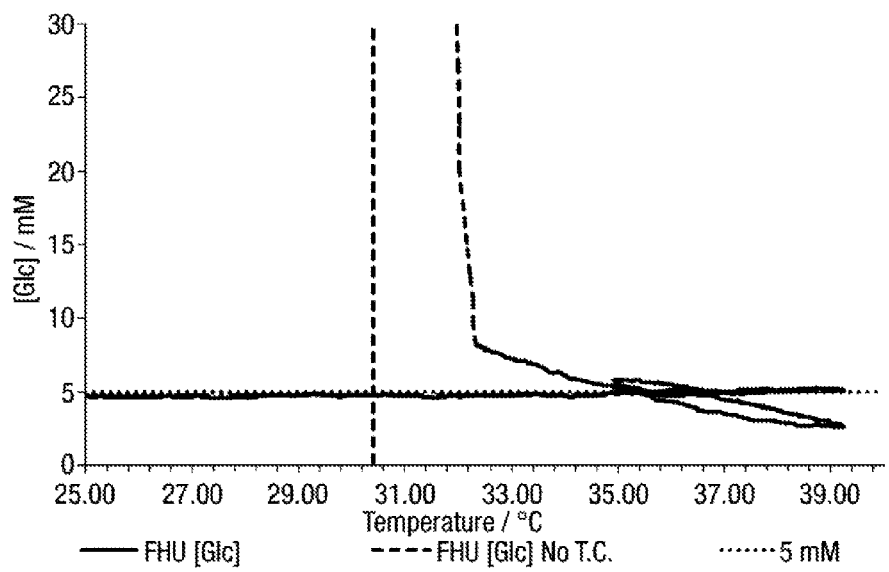
FIG. 8 shows glucose concentration vs. temperature for a calibrated sensor with and without temperature correction.
FIG. 9 shows measured glucose concentration with and without temperature compensation vs. temperature. The actual glucose concentration of the sample is 5.08 mM.

After the sensor was calibrated it was placed in a PBS solution containing glucose (5.08 mM) and the temperature was varied. The results of this are shown in FIG. 8, from which it is apparent that the accuracy of the sensor when the variable temperature calibration is applied is below 4% (32-40° C.), whereas in the case that fixed temperature calibration is carried out the error is up to 58%, FIG. 9.

The above disclosure makes reference to various specific embodiments and examples. However, it is to be understood that the claims below are in no way limited to these specific embodiments and examples.

The invention claimed is:

1. A method of calibrating a reversible-binding sensor for detecting an analyte, which method comprises:
   varying the temperature of a first calibration solution from a first temperature ($T_1$) to a second temperature ($T_2$) while the first calibration solution is in contact with a sensing region of the sensor, wherein the first temperature ($T_1$) is different than the second temperature ($T_2$);
   detecting a sensor output for each of a plurality of temperatures between the first temperature ($T_1$) and the second temperature ($T_2$) during the varying of the temperature;
   determining the sensor output for the first calibration solution as a function of temperature;
   varying the temperature of a second calibration solution from a third temperature ($T_3$) to a fourth temperature ($T_4$) while the second calibration solution is in contact with the sensing region, the second calibration solution having a concentration of analyte which is different from that of the first calibration solution, wherein the third temperature ($T_3$) is different than the fourth temperature ($T_4$);
   detecting a sensor output for each of a plurality of temperatures between the first temperature ($T_3$) and the second temperature ($T_4$) during the varying of the temperature;
   determining the sensor output for the second calibration solution as a function of temperature; and
   using the determined sensor output for the first calibration solution and the second calibration solution, each as a function of temperature, to calibrate the sensor.

2. A method according to claim 1, which further comprises:
varying the temperature of a third calibration solution from a fifth temperature ($T_5$) to a sixth temperature ($T_6$) while the third calibration solution is in contact with the sensing region, the third calibration solution having a concentration of analyte which is different from those of the first and second calibration solutions, wherein the fifth temperature ($T_5$) is different than the sixth temperature ($T_6$);

detecting a sensor output for each of a plurality of temperatures between the fifth temperature ($T_5$) and the sixth temperature ($T_6$) during the varying of the temperature; and determining the sensor output for the third calibration solution as a function of temperature;

wherein calibrating the sensor comprises using the determined sensor output for the first calibration solution, the second calibration solution, and the third calibration solution, each as a function of temperature, to calibrate the sensor.

3. A method according to claim 1, wherein $T_2$ is greater than $T_1$, $T_4$ is greater than $T_3$.

4. A method according to claim 3, wherein $T_3$ is less than or equal to $T_2$.

5. A method according to claim 1, wherein the second calibration solution is formed by mixing the first calibration solution with an amount of analyte.

6. A method according to claim 1, wherein the concentration of analyte in the first calibration solution is zero.

7. A method according to claim 1, wherein the sensor is an optical sensor.

8. A method according to claim 1, wherein the analyte is glucose.

9. A method according to claim 8, wherein a first amount of glucose is mixed with the first calibration solution to form the second calibration solution, wherein said first amount of glucose is provided in solid form, which solid form comprises alpha and beta glucose.

10. A method according to claim 1, wherein the analyte reversibly binds to a receptor within the sensing region of the sensor at an analyte:receptor ratio of 1:1.

11. A method according to claim 10, wherein the analyte is glucose and the receptor comprises a boronic acid species.

12. A method according to claim 1, which further comprises
contacting the sensing region of the sensor with a sample and determining the concentration of analyte in the sample;
wherein the time between the sensor contacting the first calibration solution and varying the temperature between the first temperature $T_1$ and the second temperature $T_2$, and the sensor contacting the sample and determining the concentration of analyte in the sample, is 24 hours or less.

13. A method according to claim 1, wherein the sensor to be calibrated is provided as part of a kit, the kit further comprising a calibration chamber and a temperature controller.

14. A method according to claim 13, wherein
the first calibration solution is present in a first compartment of the calibration chamber,
an amount of analyte is present in a second compartment of the calibration chamber,
the second compartment of the calibration chamber is initially separated from the first compartment of the calibration chamber by a water-impermeable first dividing material, and
wherein said method comprises breaking or removing the first dividing material to form the second calibration solution.

15. A method according to claim 14, wherein
the calibration chamber comprises a third compartment containing a further amount of the analyte,
the third compartment is initially separated from the remainder of the calibration chamber by a second water-impermeable dividing material, and
wherein said method comprises breaking or removing the second dividing material to form the third calibration solution.

16. A method of calibrating a reversible-binding sensor for detecting an analyte, which method comprises:
(i) varying the temperature of a first calibration solution from a first temperature ($T_1$) to a second temperature ($T_2$) while the first calibration solution is in contact with a sensing region of the sensor;
(ii) determining the sensor output for the first calibration solution as a function of temperature;
(iii) varying the temperature of a second calibration solution from a third temperature ($T_3$) to a fourth temperature ($T_4$) while the second calibration solution is in contact with the sensing region, the second calibration solution having a concentration of analyte which is different from that of the first calibration solution;
(iv) determining the sensor output for the second calibration solution as a function of temperature; and
(v) using the determined sensor output from steps (ii) and (iv) to calibrate the sensor, wherein the analyte reversibly binds to the receptor at an analyte:receptor ratio of 1:1, and step (ii) comprises:
a. fitting two or more temperatures in a temperature range from $T_1$ to $T_2$ to the following equation:

$$I = I_1 + s_1(T - T_c)$$

wherein I is the sensor output, T is the temperature, $T_c$ is the nominal calibration temperature, $I_1$ is the sensor output for the first calibration solution at $T_c$ and $s_1$ is a constant; and
b. determining $s_1$;
step (iv) comprises
a. fitting two or more temperatures in a temperature range from $T_3$ to $T_4$ to the following equation:

$$I = I_2 + s_2(T - T_c)$$

wherein I, T, and $T_c$, are as defined above, $I_2$ is the sensor output for the second calibration solution at $T_c$, and $s_2$ is a constant; and
b. determining $s_2$;
step (v) comprises
a. determining the values of temperature coefficients $\alpha$ and $\beta$ using the following equations:

$$\alpha = \frac{s_1}{I_0} \left[ \frac{1 - \frac{\rho_1}{\rho_2} \frac{s_2}{s_1} \frac{(1+\rho_2 K_a)^2}{(1+\rho_1 K_a)^2}}{1 - \frac{\rho_1}{\rho_2} \frac{(1+\rho_2 K_a)^2}{(1+\rho_2 K_a)^2}} \right]$$

$$\beta = \frac{(1+\rho_2 K_a)^2 T_c (s_2 - s_1)}{(I_\infty - I_0) \rho_2 K_a} \left[ \frac{1}{1 - \frac{\rho_1}{\rho_2} \frac{(1+\rho_2 K_a)^2}{(1+\rho_1 K_a)^2}} \right]$$

wherein $I_0$ is the sensor output for zero analyte concentration at $T_c$, $I_\infty$ is the sensor output at infinite analyte concentration, $\rho_1$ is the concentration of analyte in the first calibration solution, $\rho_2$ is the concentration of analyte in the second calibration solution, $K_a$ is the association constant for the reversible binding of receptor and analyte, and $s_1$ and $s_2$ are as determined above; and b. using $\alpha$ and $\beta$ to calibrate the sensor.

17. A method according to claim 13, wherein the kit further comprises one or more control modules, said one or more control modules being configured to contact the sensing region of the sensor with consecutive calibration solutions; monitor and/or adjust the temperature of the calibration solutions; determine sensor output as a function of temperature; and calibrate the sensor, wherein the processes recited in claim 1 are carried out using the control module.

18. A calibration system comprising one or more control modules, wherein the one or more control modules are configured to contact the sensing region of a reversible binding sensor with consecutive calibration solutions; monitor or adjust the temperature of the calibration solutions; detect a sensor output for each of a plurality of different temperatures during the varying of the temperature for each calibration solution; and determine sensor output of said sensor as a function of temperature for each of said calibration solutions.

19. A calibration system according to claim 18, wherein said one or more control modules are further configured to calibrate the sensor.

20. A calibration system according to claim 18, wherein the one or more control modules are configured to carry out a method comprising:

varying the temperature of a first calibration solution from a first temperature ($T_1$) to a second temperature ($T_2$) while the first calibration solution is in contact with a sensing region of the sensor;

determining the sensor output for the first calibration solution as a function of temperature;

varying the temperature of a second calibration solution from a third temperature ($T_3$) to a fourth temperature ($T_4$) while the second calibration solution is in contact with the sensing region, the second calibration solution having a concentration of analyte which is different from that of the first calibration solution;

determining the sensor output for the second calibration solution as a function of temperature; and using the determined sensor output for the first calibration solution and the second calibration solution, each as a function of temperature, to calibrate the sensor.

21. A calibration system according to claim 18, further comprising at least one calibration chamber.

22. A calibration system according to claim 18, further comprising a reversible binding sensor for detecting an analyte.

* * * * *

UNITED STATES PATENT AND TRADEMARK OFFICE
CERTIFICATE OF CORRECTION

| | | Page 1 of 1 |
|---|---|---|
| PATENT NO. | : 8,607,612 B2 | |
| APPLICATION NO. | : 13/686484 | |
| DATED | : December 17, 2013 | |
| INVENTOR(S) | : Nicholas Paul Barwell et al. | |

It is certified that error appears in the above-identified patent and that said Letters Patent is hereby corrected as shown below:

Title Page – Column 1, after Prior Application Data, please insert

-- Related U.S. Application Data

(63) Continuation of application No. PCT/GB2012/051188 filed on May 25, 2012.

(60) Provisional application No. 61/490,951, filed May 27, 2011, -- therefor.

Signed and Sealed this
Seventh Day of July, 2015

Michelle K. Lee
*Director of the United States Patent and Trademark Office*